United States Patent
Ebita et al.

(10) Patent No.: US 7,684,041 B2
(45) Date of Patent: Mar. 23, 2010

(54) COLOR INSPECTION SYSTEM

(75) Inventors: Takao Ebita, Fukui (JP); Norihiro Ogata, Fukui (JP); Masahiro Matsumura, Fukui (JP); Keiichirou Tabata, Fukui (JP)

(73) Assignee: Seiren Co., Ltd., Fukui-shi (JP)

( * ) Notice: Subject to any disclaimer, the term of this patent is extended or adjusted under 35 U.S.C. 154(b) by 248 days.

(21) Appl. No.: 11/795,707

(22) PCT Filed: Mar. 29, 2006

(86) PCT No.: PCT/JP2006/306414

§ 371 (c)(1),
(2), (4) Date: Sep. 25, 2007

(87) PCT Pub. No.: WO2006/106707

PCT Pub. Date: Oct. 12, 2006

(65) Prior Publication Data

US 2009/0190132 A1    Jul. 30, 2009

(30) Foreign Application Priority Data

Mar. 30, 2005  (JP)  ............................ 2005-096601

(51) Int. Cl.
*G01J 3/50*  (2006.01)
(52) U.S. Cl. .................. 356/402; 356/425; 250/226
(58) Field of Classification Search ............ 356/402, 356/405, 406, 425
See application file for complete search history.

(56) References Cited

U.S. PATENT DOCUMENTS 6,078,398 A * 6/2000 Feldman et al. ............. 356/402

FOREIGN PATENT DOCUMENTS

JP    51-099088    9/1976

(Continued)

OTHER PUBLICATIONS

M. Ronnier Luo, Colour science, The Colour Image Processing Handbook, edited by S. J. Sangwine and R.E.N. Home, (Chapman & Hall), 1998, pp. 26-66.*

(Continued)

*Primary Examiner*—F. L Evans
(74) *Attorney, Agent, or Firm*—Flynn, Thiel, Boutell & Tanis, P.C.

(57) ABSTRACT

A color inspection system capable of making a determination on pass or failure with accuracy equivalent to that for the case of a visual inspection even in the case of inspecting various textile products as measurement targets, such as raised cloth, cloth with printed patterns such as a marbled pattern, moire pattern and detailed pattern is provided. With the color inspection system, an illuminant is set to shine a light on the surface of a textile product placed on the top surface of a measuring platform to thereby make measurements from a direction at an angle of 45 degrees from the surface of a measuring region of the textile product by use of a spectroradiometer of a measuring unit. The spectroradiometer is provided with a wide range lens attached thereto to thereby expand a measuring region. The results of measurement by the spectroradiometer are inputted to an information processor of a determination unit. The information processor computes color values for the whole measuring region to be compared with standard color values stored in a memory to thereby make a determination on pass or fail.

4 Claims, 4 Drawing Sheets

FOREIGN PATENT DOCUMENTS

| | | |
|---|---|---|
| JP | 60-033020 | 2/1985 |
| JP | 08-015026 | 1/1996 |
| JP | 08-029256 | 2/1996 |
| JP | 09-203664 | 8/1997 |
| JP | 11-258049 | 9/1999 |
| JP | 2001-066187 | 3/2001 |

OTHER PUBLICATIONS

Shikisai Kidokei Bunko Hoshakei, The Industrial Coating, No. 152, 1998, pp. 36-39.

\* cited by examiner

COLOR INSPECTION SYSTEM

FIELD OF THE INVENTION

The invention relates to a color inspection system for termining whether or not a surface color of a target for inspection, such as a textile product, and so forth, is acceptable, and in particular, to a color inspection system for use in determining whether or not the dyed condition of a textile product such as a raised cloth, cloth with printed patterns such as a marbled pattern, moire pattern and detailed pattern is acceptable.

BACKGROUND OF THE INVENTION

In quality control of textile products, quality control of a surface color thereof is one of important items, and it is regarded that points of importance in controlling color are how close to a standard color the surface color is rendered, and how to decide color tolerance.

Such quality control of color has been conducted by skilled inspectors in accordance with JIS (Z 8723) in the past. However, a color inspection through visual inspection conducted by the inspector has problems such as a lack of unity between determinations made by a plurality of inspectors, and variation in determinations made by one inspector.

Accordingly, in order to cope with the problems, a proposal has been made to conduct a color inspection on textile products, using a color measuring instrument. For example, in Patent Document 1, there has been disclosed a method whereby color measuring is made of continuous lengths, such as a piece of cloth, film, sheet, and so forth, while transferring the same by use of a plurality of sensors.

In Patent Document 2, there has been disclosed a method whereby color measurement by the color element refers to a predetermined color system with reference to a plurality of images about an inspection region of an input image which is inputted by a CCD color camera, and so forth, to thereby find a frequency distribution showing a relationship between color measured values and pixel numbers, making a determination on whether or not a target for inspection is excellent in color shade by comparing the frequency distribution with a standard frequency distribution as a preset. In Patent Document 3, there has been disclosed a method whereby reflected light from a color measuring region of a predetermined area, including patterns, is received by a sectrophotometer to thereby compute the average surface color values of one kind or more, and a determination is made on whether or not a patterned fabric is acceptable on the basis of the color difference between the average surface color values and a standard value. Further, in Patent Document 4, there has been disclosed a method whereby a fabric of weaving or knitting is run, and upon detection of a mark thereof, running is stopped to press down the fabric of weaving or knitting, thereby measuring the color values by a calorimeter.

Patent Document 1 JP 08-15026 A
Patent Document 2 JP 09-203664 A
Patent Document 3 JP 60-33020 A
Patent Document 4 JP 5 1-99088 A

SUMMARY OF THE INVENTION

As shown in the Patent Documents described above, with a color inspection system for textile products, there is either a case where a measurement is carried out at a position in close proximity to a measurement target, or a case where the measurement is carried out at a position away from the measurement target. In the case of carrying out the measurement at the position in close proximity to the target for measurement, a measuring instrument such as a calorimeter and a spetrophotometer is generally used, thereby conducting the measurement with the measuring instrument in close contact with the target for measurement, so that the measurement can be implemented without being affected by ambient light. However, because a measurement region is small in size (a region 8 to 50 mm in diameter is generally set), the measurement in a plurality of regions needs be carried out in order to conduct a highly accurate inspection. In the case of products subjected to a raising treatment, and products with the printed patterns such as a marbled pattern, moire pattern and detailed pattern, in particular, there occurs a large variation in the measured value in the case of using the calorimeter and the spetrophotometer, so that it is difficult to conduct a highly accurate inspection. In the case of carrying out the measurement at a position away from the target for measurement, a CCD camera is used, and thus the measurement is prone to be affected by ambient light. As CCD elements obtain a high temperature when used for many hours, a measured value will contain a lot of noise, thereby posing a problem with respect to the precision of executing an accurate color inspection. Accordingly, this method is not suited for the case where severe quality control in color is required, as with the case of textile products.

The textile products include various types of products such as the so-called solid-dyeing type that is dyed in a single color, a parti-colored type expressing mixture of a plurality of colors in spots, a type with a flat and smooth surface, a type with an uneven surface as a result of the raising treatment, and weaving or knitting, and a type obtained by a combination thereof.

In the case of the textile product in a single color, by carrying out the color inspection, using the inspection system and the measuring instrument such as the calorimeter and the spetrophotometer, as described in the Patent Documents described above, it is possible to obtain the same result as is obtained by visual inspection with the human eyes. However, in the case of printed patterns such as a marbled pattern, moire pattern and detailed pattern, having color differentiation in a plurality of colors, there occurs a large discrepancy in inspection result between the case of the visual inspection with the human eye, and the case of inspection with the conventional inspection system. Furthermore, if asperities are formed on the surface of a textile product, the discrepancy in inspection result will become greater. For this reason, it is conceivable to measure a plurality of regions in order to enhance the reliability of the results of the inspection by use of the inspection system. However, sufficient reliability has not been obtained yet under the present circumstances.

It is therefore an objective of the invention to provide a color inspection system capable of not only enhancing the accuracy in inspection/determination, even in the case of inspecting various textile products as targets for inspection, such as a raised cloth, a cloth with printed patterns such as a marbled pattern, moire pattern and detailed pattern, and so forth, or a cloth with asperities formed on the surface thereof but also making a more accurate determination by the joint use of a visual inspection conducted in the same inspection environment.

In accordance with one aspect of the present invention, there is provided a color inspection system comprising a measurement platform used for placing a measurement target thereon, an illuminant for shining a light on the surface of the measurement target, and a measuring unit disposed away by a predetermined distance from the measurement target including a spectroradiometer used for making measurement on a measuring region on the surface of the measurement target, and a determination unit for determining whether or not a surface color of the measurement target is acceptable on the basis of measurement results obtained from the spectroradiometer. Further, the measuring unit preferably makes a measurement on the measuring region shone by a light with the spectroradiometer through the intermediary of a wide range lens. Still further, a measurement diameter of the spectroradiometer, on the measurement target, is preferably set to not less than 7 cm. Yet further, with those features, the illuminant is preferably set so as to shine a light on the measuring region from a direction substantially perpendicular thereto, and the spectroradiometer of the measuring unit is preferably set to make a measurement from a direction inclined at an angle of 45 degrees to the measuring region.

The color inspection system according to the invention is made up as described above, and in particular, the measuring unit thereof employs the spectroradiometer, so that the measurement can be made with the system disposed at a position away from the measurement target. By setting a color inspection environment equivalent to a visual inspection and setting the measurement diameter not less than 7 cm, it becomes possible to make an accurate measurement, even on patterned products and textile products subjected to a raising treatment, without being affected by color differentiation due to patterning, and asperities on the surface thereof. The spectroradiometer is an instrument for measuring spectral radiance energy distribution of light (electromagnetic waves) from the measurement target, and is used mainly for measuring radiation light from an illuminant, such as the fluorescent lamp, by the wavelength. However, with the present invention, the spectroradiometer is used for measurement of an object-color, that is, measurement of reflected light shone on an object to be selectively reflected from the surface of the object. Further, various experiments have been carried out resulting that it is possible to obtain results of determination on pass or failure of color, more accurate than in the case of the visual inspection if the spectroradiometer is used in color inspection of measurement targets such as textile products of various types in color shade and form. The colorimeter, and spetrophotometer, used in the past, are useful in carrying out color measurement of an object colored in a single color and relatively flat in surface shape. However, because those instruments need to make a measurement in close proximity to the measurement target, there is a likelihood of a deterioration in measurement precision in the case of the inspection of patterned objects and objects subjected to the raising treatment. Accordingly, color inspections with the use of various instruments have been tested obtaining information that, in the case of the spectroradiometer, noncontact inspection in a large area can be conducted, and a color shade as a whole can be measured at a position away from the surface of a patterned product and a product subjected to the raising treatment. If an inspection is carried out based on relative evaluation by comparing measurement results with standard values, it is possible to make a determination on pass or failure of color with high precision.

In this connection, as the spectroradiometer has a narrow measuring region, the same is installed at a position at least several meters away from the measurement target when measuring an object-color. However, by making measurement through the intermediary of the wide range lens, the measuring region thereof, at a position close to the measurement target, can be enlarged. Further, by setting the measurement diameter of the spectroradiometer, on the measurement target, to not less than 7 cm, more accurate measurement results having little variation can be obtained. Still further, by setting the illuminant so as to shine a light on the measuring region from the direction substantially perpendicular thereto, and setting the spectroradiometer so as to enable the measurement to be made from a direction inclined at an angle of 45 degrees to the measuring region, it becomes possible to stably obtain substantially the same result as is obtained by visual inspection with the human eyes.

Furthermore, since the spectroradiometer can make a measurement at a position away from the measurement target, an inspection using the same, in combination with a visual inspection, can be implemented with ease, so that with the combined use of both the inspections, it is possible to further enhance the precision in inspection through mutual checking of the results of the respective inspections, such as correction of variation in determination by the visual inspection, and visual checking against the results of the determination by the color inspection system.

With cloths used for automobile interior materials, in particular, asperities are often formed on the surfaces of three-dimensional structures thereof, and printed patterns, such as a marbled pattern, moire pattern and a detailed pattern or the raising treatment are often applied thereto, so that each of the cloths will not appear in a single color showing the color of a constituent material thereof as it is, rendering it difficult to obtain accurate measurement results if a measurement area is small. For this reason, with the cloths described, if respective measuring regions are increased in size to thereby make a measurement on the whole region so as to find a color shade on the average, measurement results with less variation will be obtained. According to the results of experiments carried out by the inventors, in the case of cloths commonly used for the automobile interior materials, by setting the measurement diameter of the spectroradiometer to not less than 7 cm, it was possible to obtain stable measurement results with respect to variously colored patterns.

PREFERRED EMBODIMENTS OF THE INVENTION

Embodiments of the invention are described hereinafter with reference to the accompanying drawings. Each of the embodiments described hereinafter is a preferred specific example, and has various technical particularity. However, it is to be understood that the invention is not limited to any of the details of description, unless otherwise specified.

Figure 1:
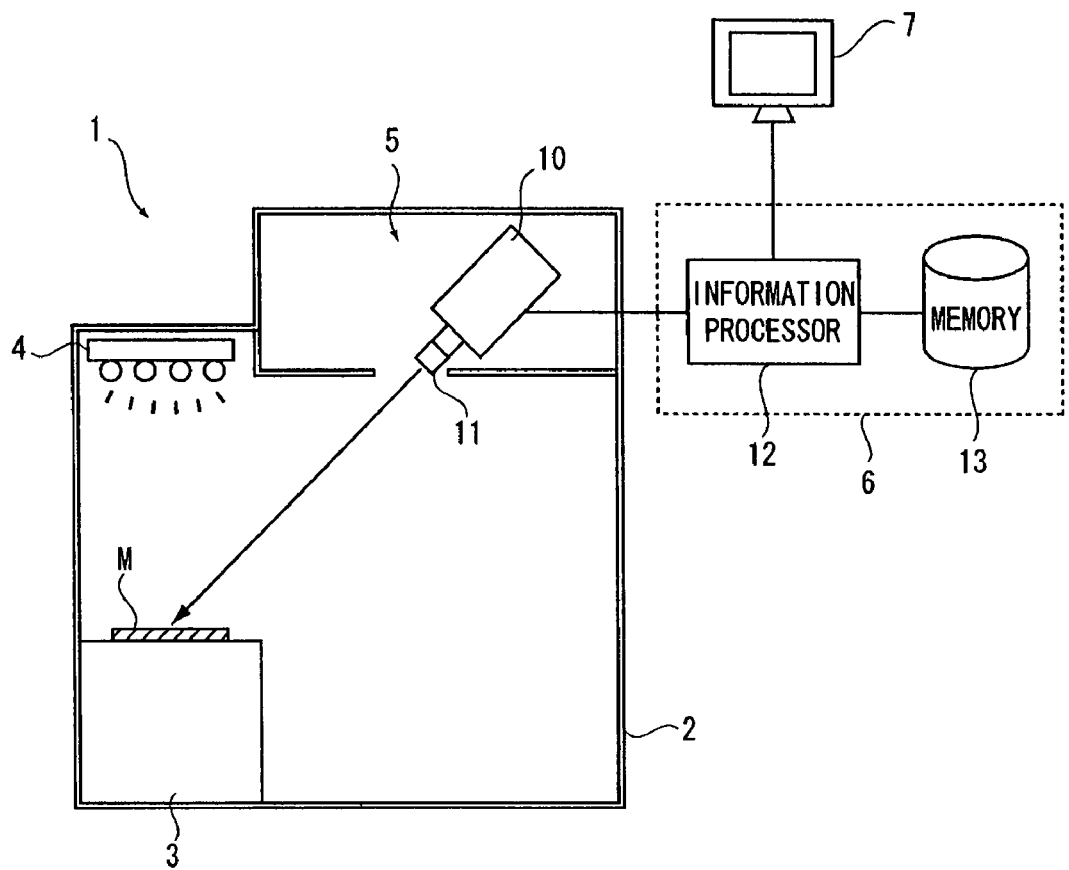
FIG. 1 is a schematic block diagram showing an embodiment of a color inspection system according to the invention.

FIG. 1 is a schematic block diagram showing an embodiment of a color inspection system according to the invention. A color inspection system 1 comprises a measurement platform 3 installed on the bottom of a dark room 2, an illuminant 4 installed above the measurement platform 3, a measuring unit 5 disposed so as to adjoin the illuminant 4, a determination unit 6 installed outside the dark room 2, for receiving measurement data from the measuring unit 5, and a display 7 for displaying the results of determination processing by the determination unit 6, and so forth.

A textile product M in sheet form, as a measurement target, is placed on the top surface of the measuring platform 3, and the top surface of the textile product M is set to be horizontal in orientation. The illuminant 4 is made of various kinds of illuminants conforming to the specification of JIS Z8720.

Figure 2:
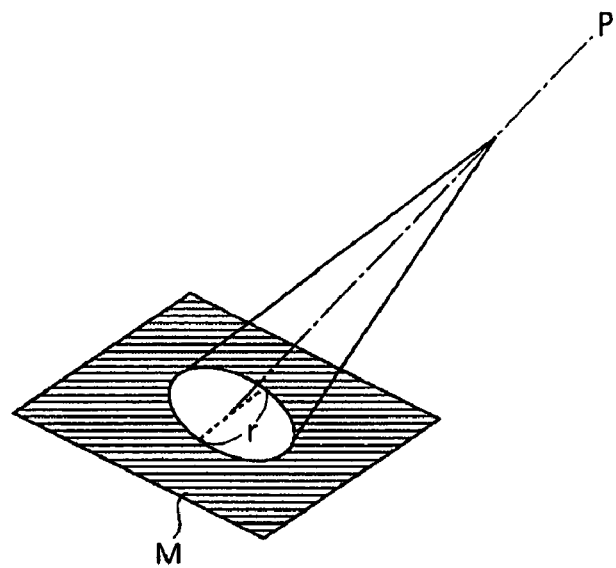
FIG. 2 is a schematic illustration concerning a measurement diameter of a spectroradiometer.

The measuring unit 5 is provided with a spectroradiometer 10, and the spectroradiometer 10 has a wide range lens 11 attached to a front face of an objective lens thereof, on which light is incident. With the spectroradiometer 10, because a measuring angle thereof is as small as in a range of 0.1 to 2.0 degrees, the measuring angle is expanded according to the size of a measuring region of the textile product M by the use of the wide range lens 11. It needs only be sufficient to use the wide range lens 11 with its focal distance—100 mm or less, and the focal distance may be adjusted as appropriate according to the size of the measuring region as set on the surface of the textile product M. By rendering the focal distance smaller, a measurement diameter corresponding to the measuring region can be enlarged. As shown in FIG. 2, the measuring region of the spectroradiometer 10 is substantially in the shape of an ellipse, and the measurement diameter thereof is defined as a diameter r along the minor axis of the ellipse centering around a point where an optical axis P of light incident on the spectroradiometer 10 intersects the surface of the measuring region.

The determination unit 6 comprises an information processor 12 for receiving the measurement data of the spectroradiometer 10, and a memory 13 for storing standard data. The information processor 12 computes color values L*, a*, b* of CIELAB color space for the measuring region in whole on the basis of spectral data of the measuring region, obtained from the spectroradiometer 10. The memory 13 prestores color values of textile products, each serving as a standard, and the information processor 12 reads the stored color values as the standards to be compared with the color values obtained from the measurement results, thereby determining whether or not the textile product subjected to measurement is acceptable. When making comparisons, it needs only be sufficient to compute a color difference value by use of the known color difference formula (for example, CIEDE 2000 color difference formula) and to set an appropriate threshold value, thereby determining the textile product M as being defective if the color difference value exceeds the threshold value. Further, the results of inspections by visual inspections conducted in the past may be accumulated, and threshold values may be set on the basis of the results of the determination on pass or failure, based on the results of the inspections. With the color inspection system according to the invention, since inspection can be made by a visual inspection with human eyes as well under the same environment as a measurement environment of the system, it is possible to confirm matching between the measurement results of the system and the results of the determination by the visual inspection, so that accuracy in the determination can be further enhanced.

The illuminant 4 is set to shine a light on the surface of the textile product M substantially evenly from a direction perpendicular thereto, and the spectroradiometer 10 is set to enable a measurement to be made from a direction at an angle of 45 degrees to the surface of the measuring region of the textile product M.

EXAMPLES

A color inspection by use of the color inspection system of a configuration shown in FIG. 1 was conducted on textile products of mottled patterns, subjected to a raising treatment. For samples, five pieces of cloths differing in color tone from each other, as shown in the respective photographs of FIGS. 6 to 10, were prepared.

Measurements were conducted with the use of a daylight fluorescent lamp at D50 in color rendering AAA as an illuminant, and a spectroradiometer (product name: SR—3) manufactured by Topcon Corp, with a wide range lens (a focal distance—150 mm) attached to the front face thereof. As a result of the wide range lens being attached to the front face, it was possible to set the size of a measuring region on the surface of a textile product to 7 cm in diameter, and to set a distance between the spectroradiometer and the textile product to 170 cm. Accordingly, as the color inspection system as a whole can be rendered more compact, the system can be unitized, thereby enabling the whole system to be easily moved.

Figure 3:
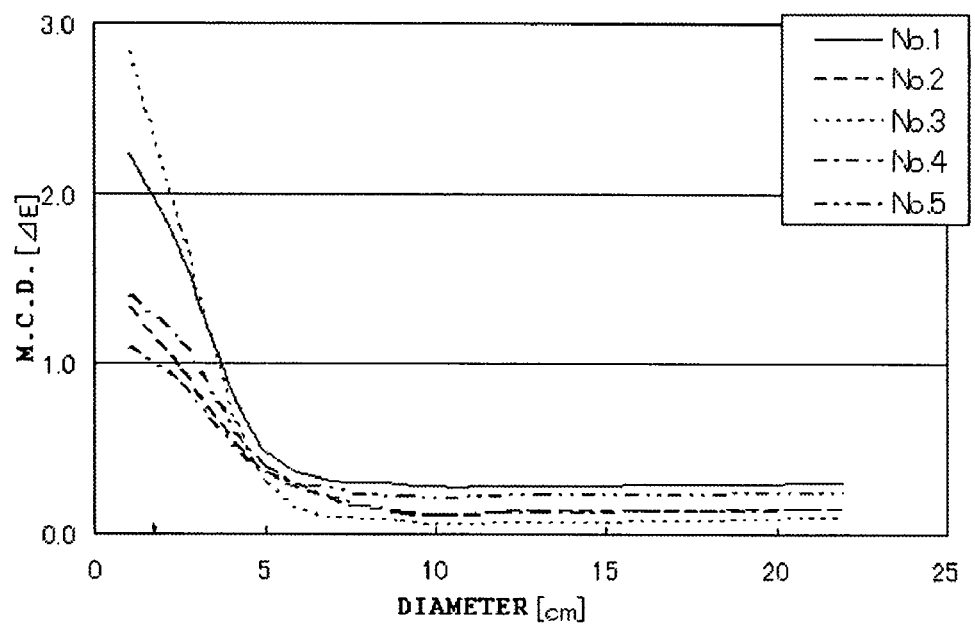
FIG. 3 is a graph showing co-relation between a maximum color difference of measurement results, and the measurement diameter in the case of a measurement inclination angle being set to 45 degrees.
Figure 4:
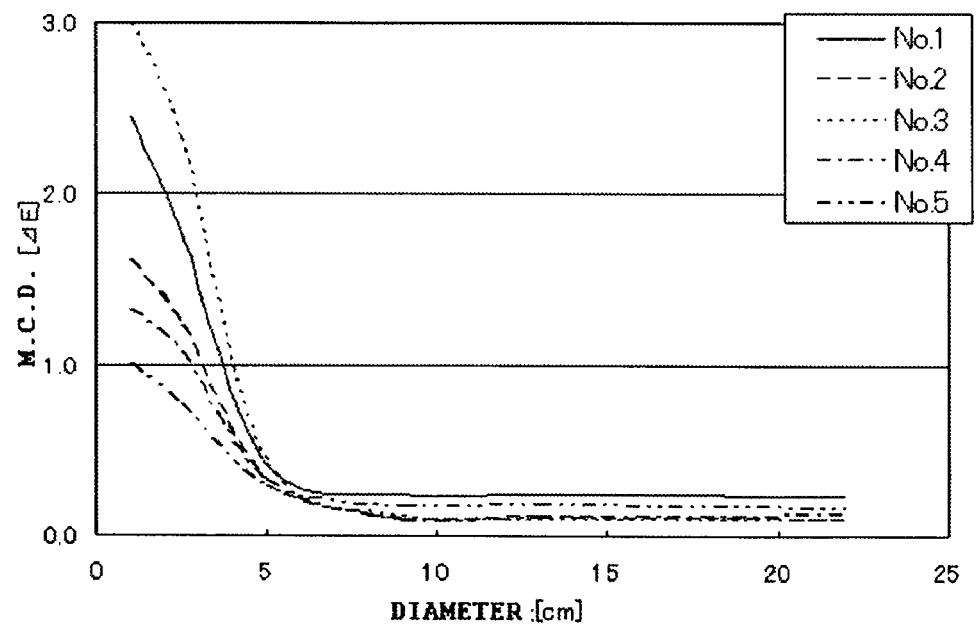
FIG. 4 is a graph showing co-relation between a maximum color difference of measurement results, and the measurement diameter in the case of a measurement inclination angle being set to 30 degrees.
Figure 5:
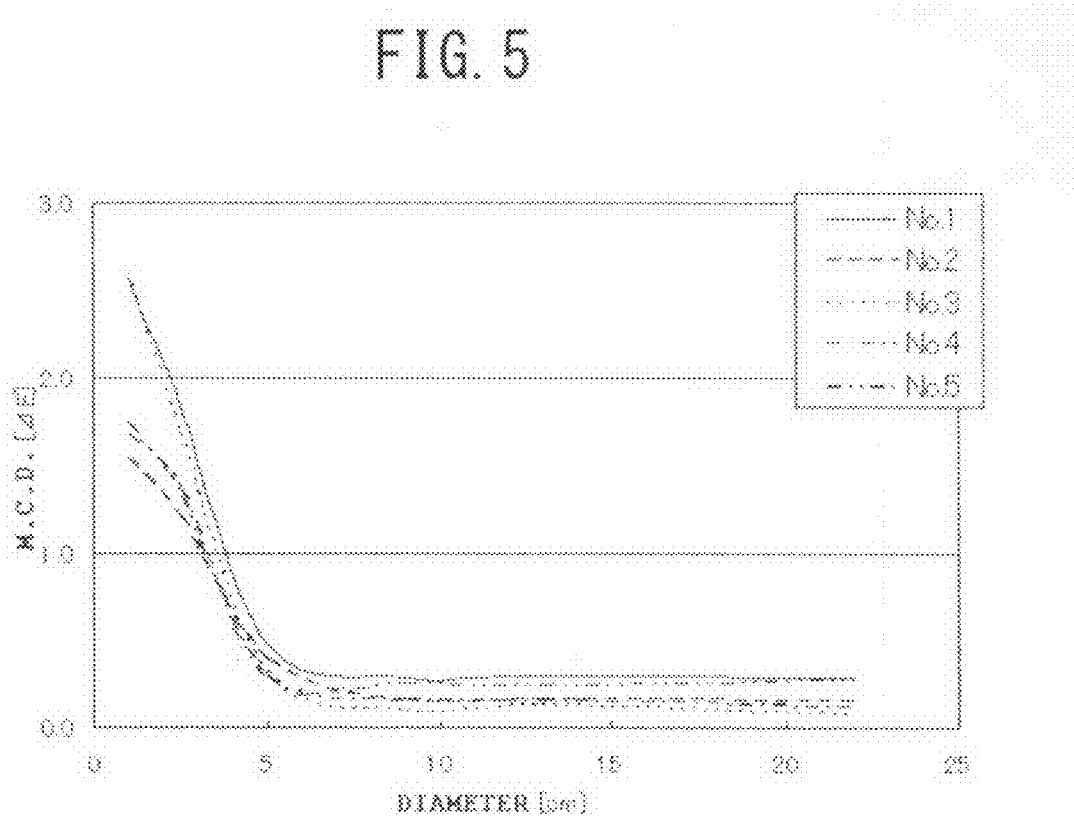
FIG. 5 is a graph showing co-relation between a maximum color difference of measurement results, and the measurement diameter in the case of a measurement inclination angle being set to 10 degrees.
Figure 6:
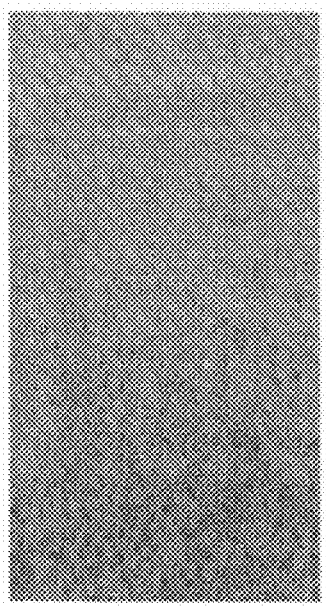
FIG. 6 is a photograph showing a textile product used as a sample.
Figure 7:
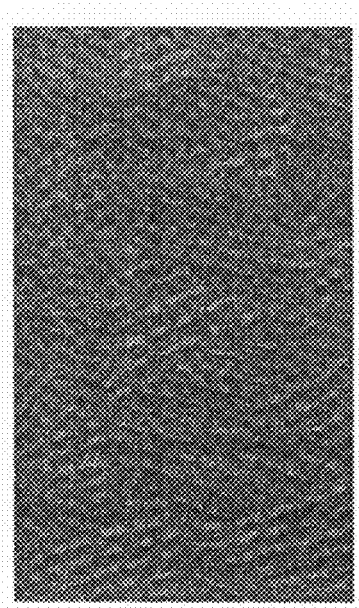
FIG. 7 is a photograph showing another textile product used as a sample.
Figure 8:
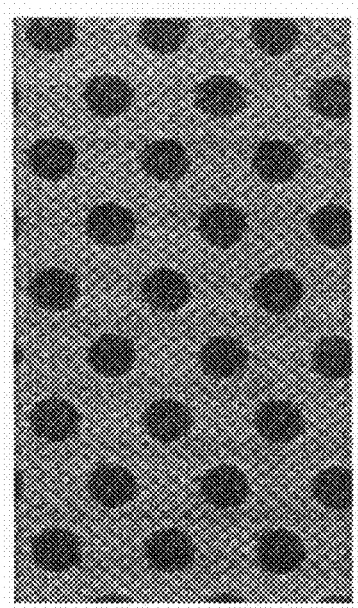
FIG. 8 is a photograph showing still another textile product used as a sample.
Figure 9:
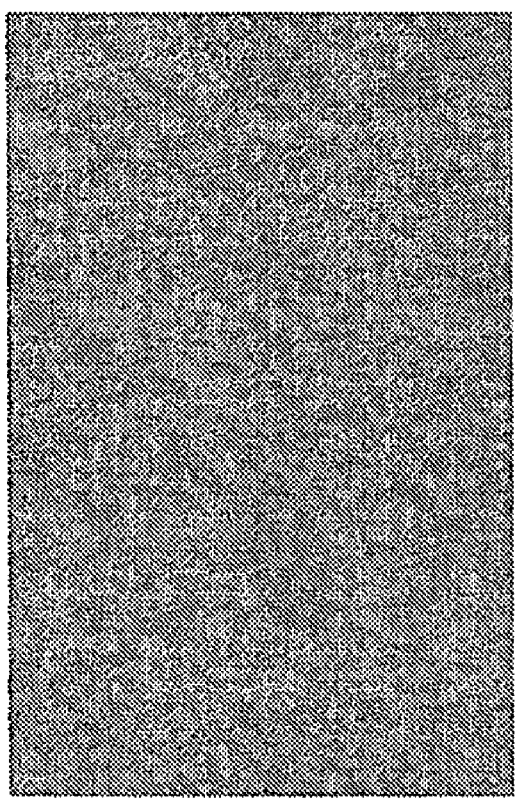
FIG. 9 is a photograph showing a further textile product used as a sample.
Figure 10:
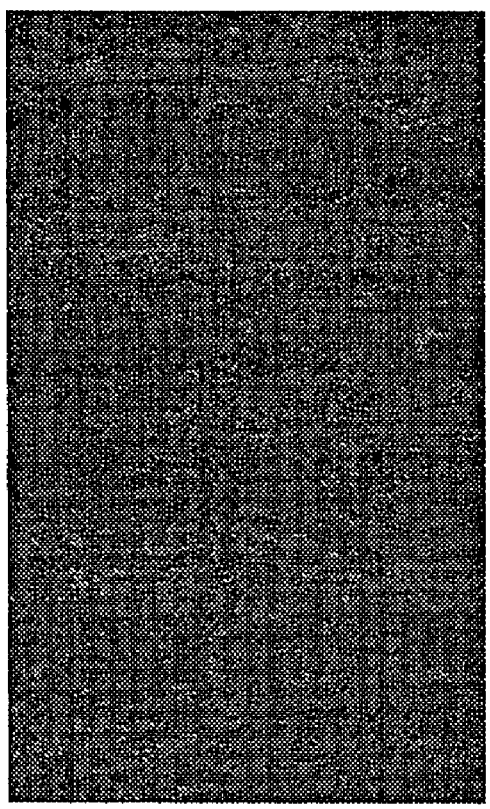
FIG. 10 is a photograph showing a still further textile product used as a sample.

A patterned color tone is applied to the surface of each of the textile products used in the inspection, subjected to the raising treatment, as shown in the respective photographs. When conducting measurements in close proximity to the measurement targets as with the case of a measurement by use of the calorimeter or the spetrophotometer, it is difficult to implement highly accurate measurements. FIGS. 3 to 5 are graphs showing the relationship between a maximum color difference in relation to a standard value, and a measurement diameter when a measurement was conducted 10 times while varying a measuring region of the textile product. A measurement inclination angle against the measurement target is set to 45, 30, and 10 degrees in FIGS. 3, 4, and 5, respectively. As is evident from FIGS. 3 to 5, with all cloths, the maximum color difference is found converging to substantially a constant value at the measurement diameter not less than 7 cm, showing that a stable measurement value can be obtained with the measurement diameter kept at not less than 7 cm, thereby enabling a highly accurate determination on pass or failure to be implemented. Thus, with the color inspection system according to the invention, measurement is carried out at a position away from the measurement target, and by adopting a wide measuring region, it becomes possible to inspect color shade of the region in whole, thereby enabling an accurate and stable determination on pass or failure to be implemented.

Now, measurements were carried out on 10 varieties of products subjected to raising treatments, in 800 lots, and visual inspections as practiced in the past were also carried out on the same products. Then, matching between respective results of the measurements and respective results of the visual inspections was reviewed, and the results of such reviewing are shown in Table 1.

TABLE 1

| case | content | matching |
|---|---|---|
| 1 | measurement results (good)/visual inspection results (good) | 83% |
| 2 | measurement results (good)/visual inspection results (no) | 3% |
| 3 | measurement results (no)/visual inspection results (good) | 2% |
| 4 | measurement results (no)/visual inspection results (no) | 12% |

The matching between the respective results of the measurements and the respective results of the visual inspections adds up to 95% (case 1: 83%+case 4: 12%=95%), so that it was possible to obtain the results of the measurements and the results of the visual inspections, substantially in agreement with each other. Based on the above, it is evident that with the use of the color inspection system according to the invention, it is possible to make substantially the same determination on pass or failure as for the case of the visual inspection conducted in the past.

Cloths used for automobile interior materials are worked on so as to have surfaces with asperities formed thereon, printed patterns such as a marbled pattern, moire pattern and detailed pattern, or raising treatment applied thereto in order to enhance the decorative effects. In the case of conducting a color inspection on those cloths, it is effective to adopt a wide measuring region to thereby capture the color as a color at a glance. Upon examination of the reproducibility of the measurements on the cloths actually used for the automobile interior materials, by varying the measurement diameter of a measuring region, it was possible to confirm that stable reproducibility at 90% or higher could be obtained with a measurement diameter not less than 7 cm, as with the above-described results of the measurements. Herein, the reproducibility of the color inspection refers to the case where there exists matching between the results of the measurement by the color inspection system according to the invention, and the results of the visual inspection.

What is claimed is:

1. A color inspection system comprising:
    a measurement platform for placing a measurement target thereon;
    an illuminant for shining light on a surface of the measurement target;
    a measuring unit disposed away by a predetermined distance from the measurement target, the measuring unit including a spectroradiometer for making measurements on measuring regions on the surface of the measurement target, the spectroradiometer having a wide range lens attached to a front face of an objective lens of the spectroradiometer; and
    a determination unit for determining whether or not a surface color of the measurement target is acceptable on a basis of measurement results obtained from the spectroradiometer,
    wherein the measuring unit makes the measurements on the measuring regions shone by the light with the spectroradiometer through an intermediary of the wide range lens, and a measurement diameter of the spectroradiometer on the measurement target is preferably set to not less than 7 cm.

2. The color inspection system according to claim 1, wherein the illuminant is set to shine the light on the measuring regions from a direction substantially perpendicular thereto.

3. The color inspection system according to claim 1, wherein the spectroradiometer is set to make the measurements from a direction inclined at an angle of 45 degrees to the measuring regions.

4. The color inspection system according to claim 1, wherein the measuring target includes a raised cloth, a cloth with printed patterns or a cloth with asperities formed on the surface of the measuring target.

* * * * *